United States Patent
Lucá

[11] Patent Number: 5,242,697
[45] Date of Patent: Sep. 7, 1993

[54] METHOD OF PREPARING NUTRIFIED FOOD PRODUCTS

[76] Inventor: Maurizio Lucá, Corso Francis, 206 Int. 7, Rome, Italy

[21] Appl. No.: 896,718

[22] Filed: Jun. 10, 1992

Related U.S. Application Data

[63] Continuation-in-part of Ser. No. 604,665, Oct. 26, 1990, Pat. No. 5,132,113.

[51] Int. Cl.$^5$ ............................................. A23J 1/00
[52] U.S. Cl. ................................. 426/231; 426/648; 426/656
[58] Field of Search .................... 426/231, 656, 648

[56] References Cited

U.S. PATENT DOCUMENTS

| | | | |
|---|---|---|---|
| 3,697,287 | 10/1972 | Winitz | 426/656 |
| 3,888,996 | 6/1975 | Turro et al. | 426/62 |
| 4,225,628 | 9/1980 | Lynn | 426/549 |
| 5,064,674 | 11/1991 | Girsh | 426/585 |
| 5,132,113 | 7/1992 | Lucá | 426/72 |

*Primary Examiner*—George Yeung
*Attorney, Agent, or Firm*—Hedman, Gibson & Costigan

[57] ABSTRACT

A method of preparing a nutrified food product is disclosed, wherein the content of essential amino acids in a food is determined and an amount of essential amino acids is added to the food to form a nutrified food product having for each 10 grams of essential amino acids the following amounts of essential amino acids:
(a) from 0.608 g. to 2.470 g. isoleucine;
(b) from 0.913 g. to 4.102 g. leucine;
(c) from 0.630 g. to 3.538 g. lysine;
(d) from 0.116 g. to 1.167 g. methionine;
(e) from 0.421 g. to 1.971 g. phenylalanine;
(f) from 0.485 g. to 1.930 g. threonine;
(g) from 0.104 g. to 0.700 g. tryptophan; and
(h) from 0.630 g. to 2.850 g. valine.

14 Claims, No Drawings

METHOD OF PREPARING NUTRIFIED FOOD PRODUCTS

This application is a continuation-in-part of Ser. No. 07/604,665, filed Oct. 26, 1990 which is now U.S. Pat. No. 5,132,113.

BACKGROUND OF THE INVENTION

Human nutrition requires a source of the components of protein, carbohydrates, lipids, vitamins and minerals. Many and varied sources for these nutrient materials have been utilized in the prior art. The prior art does not disclose the concept of providing a balanced supply of nutrients which permits substantially improved absorption of the nutrients which are administered to an individual.

For some time now, it has been apparent that the solution to the world's requirement for a nourishing food supply will partly depend on maximizing the combined benefits from food technology and nutritional knowledge, and adapting these benefits toward human needs. Among the nutritional interventions to be considered in a nutritional program is food nutrification, defined as the addition of one or more nutrients to one or more commonly consumed foods or food mixtures. If properly introduced and controlled, it can improve the dietary intake of a given population. The process of "nutrification" simply makes a food more nutritious. Over the past two decades, a number of articles have been published on the merit of nutrification of foods. Nutrification is the most rapidly applied, most flexible, and most socially acceptable intervention method of changing the nutrient intake of a given population without a vast educational effort or change in the current food intake pattern. However, the tremendous potential offered by wise utilization of industrially produced nutrients, vitamins, minerals, amino acids, and protein isolates has rarely been fully utilized. The present invention provides amino acid supplements that are specially prepared for different foods. Each supplement is formulated to substantially improve the nutritional value of a given food's protein. The nutrification concept of the invention has been proven with bovine milk and soybean flour.

U.S. Pat. No. 3,697,287 disclose an amino acid food composition which is described as a palatable mixture of the essential and non-essential amino acids, minerals, vitamins, carbohydrates and fats. That composition contains essential and non-essential amino acids. The essential amino acids in such a composition are present in the following ratios:

|                 |      |
|-----------------|------|
| L-valine        | 1.0  |
| L-arginine      | 1.77 |
| L-isoleucine    | .91  |
| L-lysine        | 1.03 |
| L-phenylalanine | 1.03 |
| L-histidine     | .44  |
| L-leucine       | 1.43 |
| L-methionine    | .93  |
| L-threonine     | .91  |
| L-tryptophan    | .28  |

I have discovered that the addition of certain amino acids to food compositions to provide a resulting specific proportion of the essential amino acids will make possible a higher NNU as compared to an unnutrified food.

It is also an object of the invention to provide an improved amino acid modified nutrient composition.

It is also an object of the invention to provide an amino acid modified composition for use as a supplement, source and/or complement to foodstuffs such as flours, dry milk solids, casein liquids, soft drinks, alcoholic drinks and the like to provide or increase the net nitrogen utilization (NNU).

It is also an object of the invention to provide an amino acid modified composition which has a ratio of essential amino acids that will provide a higher net nitrogen utilization (NNU) as compared to unnutrified foods.

These and other objects of the invention will become apparent from the appended specification.

SUMMARY OF THE INVENTION

The invention comprises a novel method of enhancing the nutritional value of foods by the addition of specific amounts of essential amino acids to foods. Each food will require different amounts of essential amino acids based on the essential amino acid content of the food which is nutrified. This process of nutrification is based on the addition of a complementary quantity of essential amino acids which when combined with the quantity of essential amino acids which are present in the particular food will provide a product that will contain a total quantity of essential amino acids which will approximate the amounts of essential amino acids which are set forth in the following formula:

|               |             |
|---------------|-------------|
| isoleucine    | 0.608–2.470 |
| leucine       | 0.913–4.102 |
| lysine        | 0.630–3.538 |
| methionine    | 0.116–1.167 |
| phenylalanine | 0.421–1.971 |
| threonine     | 0.485–1.930 |
| tryptophan    | 0.104–0.700 |
| valine        | 0.630–2.850 | in amounts relative to one another which will provide a net nitrogen utilization (NNU) which is measurably higher than the unnutrified food. The composition may also contain added carbohydrates and essential Fatty Acid (EFA) sources, vitamins and/or minerals.

The nutrified compositions may have a total quantity of 1 Kcal to 250 Kcal per gram of amino acids.

The preferred ranges of protein free carbohydrate and highly polyunsaturated vegetable fat are 0–99 wt. %, protein-free carbohydrate and 99–0 wt. % highly polysaturated vegetable fat.

The nutrified compositions of the invention provide a higher Net Nitrogen Utilization than the base food material which has not been nutrified according to the invention. The specific nutrified foods of the invention which contain added carbohydrate and polyunsaturated vegetable fat have particular use in providing energy and Essential Fatty Acids (EFA), for prevention or treatment of Protein-Calorie Malnutrition (PCM). In particular, these compositions may be used when further energy and EFA intake is required, and specifically as a source of amino acid and calorie intake for supportive nutrition in the case of cancer, AIDS, trauma due to burns, surgery or in disease, such as renal disorders, liver disorders, diabetes mellitus, gout, and the like.

DETAILED DESCRIPTION OF THE INVENTION

The nutrified food of the invention is based on the addition of amino acids in specific relative amounts which provide an increased net nitrogen utilization (NNU).

Using this parameter of evaluation, it is possible using the compositions and methods of the present invention to obtain a higher NNU.

The higher NNU is believed to be obtained because of the extremely high absorption rates that are possible because of the particular compositions devised by the applicant.

The nutrified food compositions of the invention comprise those having the following proportions of amino acids in grams per 10 grams of amino acid content which are provided from the amino acid content of the food base and exogenously added amino acids:

(a) from 0.608 to 2.470 isoleucine;
(b) from 0.913 to 4.102 leucine;
(c) from 0.630 to 3.538 lysine;
(d) from 0.116 to 1.167 methionine;
(e) from 0.421 to 1.971 phenylalanine;
(f) from 0.485 to 1.930 threonine;
(g) from 0.104 to 0.700 tryptophan; and
(h) from 0.630 to 2.850 valine.

| (I) | |
|---|---|
| isoleucine | 0.730–2.470 |
| leucine | 1.096–4.102 |
| lysine | 0.756–3.538 |
| methionine | 0.139–1.167 |
| phenylalanine | 0.506–1.971 |
| threonine | 0.582–1.930 |
| tryptophan | 0.125–0.700 |
| valine | 0.756–2.850 |
| (II) | |
| isoleucine | 0.730–2.306 |
| leucine | 1.096–3.829 |
| lysine | 0.756–3.303 |
| methionine | 0.139–1.089 |
| phenylalanine | 0.506–1.840 |
| threonine | 0.582–1.802 |
| tryptophan | 0.125–0.654 |
| valine | 0.756–2.660 |
| (III) | |
| isoleucine | 0.852–2.306 |
| leucine | 1.279–3.829 |
| lysine | 0.882–3.303 |
| methionine | 0.162–1.089 |
| phenylalanine | 0.590–1.840 |
| threonine | 0.679–1.802 |
| tryptophan | 0.146–0.654 |
| valine | 0.882–2.660 |
| (IV) | |
| isoleucine | 0.852–2.141 |
| leucine | 1.279–3.555 |
| lysine | 0.882–3.067 |
| methionine | 0.162–1.011 |
| phenylalanine | 0.590–1.708 |
| threonine | 0.679–1.673 |
| tryptophan | 0.146–0.607 |
| valine | 0.882–2.470 |
| (V) | |
| isoleucine | 0.974–2.141 |
| leucine | 1.462–3.555 |
| lysine | 1.008–3.067 |
| methionine | 0.186–1.011 |
| phenylalanine | 0.674–1.708 |
| threonine | 0.776–1.673 |
| tryptophan | 0.166–0.607 |
| valine | 1.008–2.470 |
| (VI) | |
| isoleucine | 0.974–1.976 |
| leucine | 1.462–3.282 |
| lysine | 1.008–2.831 |
| methionine | 0.186–0.934 |
| phenylalanine | 0.674–1.577 |
| threonine | 0.776–1.544 |
| tryptophan | 0.166–0.560 |
| valine | 1.008–2.280 |
| (VII) | |
| isoleucine | 1.095–1.976 |
| leucine | 1.644–3.282 |
| lysine | 1.134–2.831 |
| methionine | 0.209–0.934 |
| phenylalanine | 0.759–1.577 |
| threonine | 0.873–1.544 |
| tryptophan | 0.187–0.560 |
| valine | 1.134–2.280 |
| (VIII) | |
| isoleucine | 1.095–1.812 |
| leucine | 1.644–3.008 |
| lysine | 1.134–2.595 |
| methionine | 0.209–0.856 |
| phenylalanine | 0.759–1.445 |
| threonine | 0.873–1.416 |
| tryptophan | 0.187–0.514 |
| valine | 1.134–2.090 |
| (IX) | |
| isoleucine | 1.217–1.812 |
| leucine | 1.827–3.008 |
| lysine | 1.260–2.595 |
| methionine | 0.232–0.856 |
| phenylalanine | 0.843–1.445 |
| threonine | 0.970–1.416 |
| tryptophan | 0.208–0.514 |
| valine | 1.260–2.090 |
| (X) | |
| isoleucine | 1.217–1.647 |
| leucine | 1.827–2.735 |
| lysine | 1.260–2.359 |
| methionine | 0.232–0.778 |
| phenylalanine | 0.843–1.314 |
| threonine | 0.970–1.287 |
| tryptophan | 0.208–0.467 |
| valine | 1.260–1.900 |
| (XI) | |
| isoleucine | 1.217–1.530 |
| leucine | 1.827–2.735 |
| lysine | 1.260–2.078 |
| methionine | 0.232–0.778 |
| phenylalanine | 0.934–1.314 |
| threonine | 0.970–1.287 |
| tryptophan | 0.208–0.467 |
| valine | 1.391–1.900 |
| (XII) | |
| isoleucine | 1.251–1.647 |
| leucine | 1.846–2.130 |
| lysine | 2.023–2.359 |
| methionine | 0.490–0.778 |
| phenylalanine | 0.843–1.144 |
| threonine | 1.053–1.287 |
| tryptophan | 0.238–0.401 |
| valine | 1.260–1.426 |
| (XIII) | |
| isoleucine | 1.289–1.647 |
| leucine | 1.917–2.130 |
| lysine | 2.023–2.359 |
| methionine | 0.490–0.778 |
| phenylalanine | 0.843–1.144 |
| threonine | 1.053–1.217 |
| tryptophan | 0.238–0.319 |
| valine | 1.342–1.426 |
| (XIV) | |
| isoleucine | 1.251–1.408 |
| leucine | 1.846–2.054 |
| lysine | 2.086–2.359 |
| methionine | 0.621–0.778 |
| phenylalanine | 0.969–1.144 |
| threonine | 1.106–1.287 |
| tryptophan | 0.293–0.401 |
| valine | 1.260–1.422 |
| (XV) | |

| | |
|---|---|
| isoleucine | 1.372–1.530 |
| leucine | 1.827–2.539 |
| lysine | 1.550–2.078 |
| methionine | 0.490–0.708 |
| phenylalanine | 0.969–1.177 |
| threonine | 0.970–1.157 |
| tryptophan | 0.208–0.373 |
| valine | 1.422–1.600 |
| (XVI) | |
| isoleucine | 1.217–1.530 |
| leucine | 1.952–2.735 |
| lysine | 1.260–1.999 |
| methionine | 0.232–0.778 |
| phenylalanine | 0.934–1.314 |
| threonine | 1.043–1.287 |
| tryptophan | 0.266–0.467 |
| valine | 1.391–1.900 |
| (XVII) | |
| isoleucine | 1.372–1.445 |
| leucine | 2.192–2.539 |
| lysine | 1.550–1.770 |
| methionine | 0.490–0.642 |
| phenylalanine | 0.969–1.155 |
| threonine | 0.970–1.052 |
| tryptophan | 0.282–0.319 |
| valine | 1.486–1.571 |
| (XVIII) | |
| isoleucine | 1.451–1.530 |
| leucine | 1.827–1.846 |
| lysine | 2.020–2.078 |
| methionine | 0.490–0.642 |
| phenylalanine | 0.969–1.144 |
| threonine | 1.115–1.157 |
| tryptophan | 0.368–0.373 |
| valine | 1.422–1.483 |
| (XIX) | |
| isoleucine | 1.328–1.357 |
| leucine | 1.917–1.951 |
| lysine | 2.086–2.250 |
| methionine | 0.642–0.673 |
| phenylalanine | 0.969–1.144 |
| threonine | 1.196–1.287 |
| tryptophan | 0.333–0.340 |
| valine | 1.342–1.422 |
| (XX) | |
| isoleucine | 1.366–1.408 |
| leucine | 1.846–1.917 |
| lysine | 2.267–2.359 |
| methionine | 0.674–0.778 |
| phenylalanine | 0.969–1.144 |
| threonine | 1.106–1.157 |
| tryptophan | 0.311–0.333 |
| valine | 1.260–1.313 |
| (XXI) | |
| isoleucine | 1.289–1.647 |
| leucine | 1.917–2.130 |
| lysine | 2.023–2.359 |
| methionine | 0.622–0.778 |
| phenylalanine | 0.843–0.988 |
| threonine | 1.053–1.271 |
| tryptophan | 0.238–0.298 |
| valine | 1.342–1.426 |
| (XXII) | |
| isoleucine | 1.251–1.328 |
| leucine | 1.950–2.067 |
| lysine | 2.078–2.315 |
| methionine | 0.490–0.689 |
| phenylalanine | 0.969–1.144 |
| threonine | 1.106–1.152 |
| tryptophan | 0.282–0.401 |
| valine | 1.306–1.422 |

Preferred compositions include the following proportions by weight of the amino acids:

| | |
|---|---|
| (XXIIII) | |
| isoleucine | 1.217–1.477 |
| leucine | 2.281–2.735. |
| lysine | 1.332–1.999 |
| methionine | 0.232–0.608 |
| phenylalanine | 0.934–1.136 |
| threonine | 1.043–1.287 |
| tryptophan | 0.304–0.467 |
| valine | 1.391–1.900 |
| (XXIV) | |
| isoleucine | 1.408–1.530 |
| leucine | 1.952–2.077 |
| lysine | 1.260–1.521 |
| methionine | 0.674–0.778 |
| phenylalanine | 1.257–1.314 |
| threonine | 1.106–1.146 |
| tryptophan | 0.266–0.373 |
| valine | 1.581–1.700 |

The especially preferred compositions include those having the following proportions by weight:

| | (I) | (II) | (III) | (IV) | (V) | (VI) | (VII) | (VIII) |
|---|---|---|---|---|---|---|---|---|
| isoleucine | 1.438 | 1.482 | 1.310 | 1.341 | 1.381 | 1.311 | 1.443 | 1.484 |
| leucine | 2.287 | 1.963 | 2.053 | 1.922 | 1.891 | 1.951 | 2.226 | 1.832 |
| lysine | 1.650 | 1.428 | 2.189 | 2.144 | 2.297 | 2.266 | 1.760 | 2.064 |
| methionine | 0.283 | 0.699 | 0.621 | 0.651 | 0.682 | 0.752 | 0.556 | 0.580 |
| phenylalanine | 0.943 | 1.288 | 1.029 | 1.027 | 1.029 | 0.959 | 1.100 | 1.067 |
| threonine | 1.226 | 1.111 | 1.107 | 1.211 | 1.113 | 1.119 | 1.041 | 1.136 |
| tryptophan | 0.448 | 0.368 | 0.293 | 0.338 | 0.318 | 0.256 | 0.317 | 0.371 |
| valine | 1.721 | 1.656 | 1.390 | 1.358 | 1.284 | 1.376 | 1.553 | 1.461 |

It is possible to substitute cysteine for part of the methionine component; and to substitute tyrosine for part of the phenylalanine component.

The nutrified foods may be used in all patients where it is desirable or necessary to avoid increasing the Blood Urea Nitrogen (BUN).

The nutrified foods of the invention have particular use during pregnancy because the proper requirement of protein is supplied without increasing Blood Urea Nitrogen (BUN) or other nitrogen metabolic residuals; in addition, its use prevents nutritional and metabolic disorders and their consequences during pregnancy and lactation.

The amount of the nutrified compositions to be used in each particular condition may generally be determined by titration of individual patients to obtain the desired nutritional response or by use of the nutrified foodstuffs in the usual amounts consumed by humans. The preferred route of administration is orally via normal feeding. The nutrified food may be administered dry as a powder, in capsules or tablets, as a solution or dispersion in a suitable liquid, or in a semi-solid medium.

It is to be understood that one or more of the mineral-free, protein-free carbohydrates may be used with one or more of the highly polyunsaturated vegetable fats as an additive to the food composition to provide the desired flavor and calorie content. Distilled water or any other suitable diluent may be added, as desired.

If desired, the invention may be used to prepare a supplement/replacement compositions for use in providing and/or enhancing a basic source of nutrition for infants, children and adults. It is of particular utility in geriatric patients and may be used as an additive for soups, gravies and the like for the prevention and treatment of Protein-Calorie-Malnutrition (PCM) while avoiding hyperuricemia, hypercholesterolemia, and elevated BUN levels.

The amount of the composition to be used in each particular condition may generally be determined in accordance of the energetic need of individual patients to obtain that desired nutritional response. The preferred route is the oral route, but a tube may be used for direct infusion into the alimentary tract.

The natural food which may be nutrified according to the present invention include liquid bovine milk and dried bovine milk products, flours derived from wheat, soybeans, rice, corn, amaranth, cous-cous, oats, rye, barely, potatoes, millet, legumes and mixtures thereof. The legumes include the edible beans, peas, chick peas, lentils and the like. Bovine sources of milk include ruminants such as domestic cattle, sheep, oxen, goats and the like. The liquid or dried milk products may be treated to remove all or a portion of the fat or lactose content in accordance with standard techniques.

EXAMPLE

The study population comprised thirty healthy subjects, fifteen men and fifteen women, with a mean age of 27 years (SD=5; range: 22–38), a mean height of 163 cm (SD=8; range: 148–174), and a mean weight of 54.1 Kg(SD=9.7; range: 39–66.5).

The subjects were selected if they satisfied all the inclusion criteria and none of the exclusion criteria. The inclusion criteria were: (a) good health; (b) age between 21 and 40 years; (c) either male or female subjects. The exclusion criterias were: (a) being under-weight; (b) pregnancy or lactation; (c) current disease which could alter the N balance; (d) phenylketonuria.

All subjects provided informed consent to participate in the study.

The fifteen men and fifteen women selected were randomly integrated, according to sex and number, into five matched groups of three men and three women, identified as groups 1, 2, 3, 4 and 5. The ages, heights and ideal weights of the subjects by groups are shown in Table I.

The study was carried out during a 100-day period, in double-blind conditions, using a quintuple cross-over technique. This technique was performed based on the known fact that N retention efficiency is increased by prior lower protein intake. This technique allowed each subject to receive the same five N source diets in different sequences.

The study was divided into the following two phases: (a) The preliminary phase was conducted during a 30-day period to equalize and stabilize the subjects' protein and energy metabolism, thus avoiding different metabolism degrees which could affect the N balances during the main phase of the study. To achieve this, the thirty subjects were fed with a composition of Table A in accordance with the "Metabolism Equalizing & Stabilizing Diet" (MESD), according to the obligatory diet sequence (Table II).

The composition of the formula in grams per 10 grams of amino acids was:

TABLE A

| | |
|---|---|
| Ile | 1.438 |
| Leu | 2.281 |
| Lys | 1.650 |
| Met | 0.283 |
| Phe | 0.943 |
| Thr | 1.226 |
| Trp | 0.448 |
| Val | 1.721 |

(b) The main phase was conducted during five consecutive 2 week periods (70 days), at which time the subjects' N balances were assessed to determine their NNU of consumed protein or amino acid formula during the periods of diets G, H, I, J and K.

Groups 1, 2, 3, 4 and 5 were fed with diets G, H, I, J and K following the obligatory sequence (Table II).

The diets consisted of an identical composition of equal amounts of protein or amino acids, carbohydrate(s), fat(s), vitamins and minerals, and had the following characteristics:

Diet "G" provided each subject with a protein intake of 0.4 g/Kg/day (equivalent to 64 mg/Kg/day of nitrogen) through dried bovine milk (Table B-1), plus an energy intake of 50 Kcal/Kg/day through essentially protein-free carbohydrate(s) and fat(s) (Table III).

Diet "H" provided each subject with a protein intake of 0.4 g/Kg/day (equivalent to 64 mg/Kg/day of nitrogen) through a nutrified dried bovine milk, (Table B-2) plus an energy intake of 50 Kcal/Kg/day through essentially protein-free carbohydrate(s) and fat(s) (Table III).

TABLE B

| | 1<br>Essential Amino Acid Composition of Dried Bovine Milk*<br>(g/10 g of essential amino acid content) | 2<br>Added Amino Acid Complement<br>(g added/10 g of essential amino acid content) |
|---|---|---|
| isoleucine | 1.443 | 0 |
| leucine | 2.226 | 0.061 |
| lysine | 1.760 | 0 |
| methionine | 0.556 | 0 |
| phenylalanine | 1.100 | 0 |
| threonine | 1.041 | 0.185 |
| tryptophan | 0.317 | 0.131 |
| valine | 1.553 | 0.168 |

*Based on the data presented in Orr, M. L., and Watt, B. K., "Amino Acid Content of Foods", U.S. Dept. Agr., 1957.

Diet "I" provided each subject with a protein intake of 0.4 g/Kg/day (equivalent to 64 mg/Kg/day of nitrogen) through soybean flour (Table C-1), plus an energy intake of 50 Kcal/Kg/day through essentially protein-free carbohydrate(s) and fat(s) (Table III).

Diet "J" provided each subject with a protein intake of 0.4 g/Kg/day (equivalent to 64 mg/Kg/day of nitrogen) through a nutrified soybean flour, (Table C-2) plus an energy intake of 50 Kcal/Kg/day through essentially protein-free carbohydrate(s) and fat(s) (Table III).

TABLE C

| | 1<br>Essential Amino Acid Composition of Soybean Flour**<br>(g/10 g of essential amino acid content) | 2<br>Added Amino Acid Complement<br>(g added/10 g of essential amino acid content) |
|---|---|---|
| isoleucine | 1.548 | 0 |
| leucine | 2.220 | 0.067 |
| lysine | 1.819 | 0 |
| methionine | 0.386 | 0 |
| phenylalanine | 1.423 | 0 |
| threonine | 0.691 | 0.535 |
| tryptophan | 0.396 | 0.052 |
| valine | 1.511 | 0.210 |

**Based on the data presented in Orr, M. L., and Watt, B. K., "Amino Acid Content of Foods", U.S. Dept. Agr., 1957.

Diet "K" provided each subject with a protein intake of 0.4 g/Kg/day (equivalent to 64 mg/Kg/day of nitrogen) through the essential amino acid formula of Table A plus an energy intake of 50 Kcal/Kg/day through essentially protein-free carbohydrate(s) and fat(s) (Table III).

The MESD, G, H, I, J and K diets were supplemented with vitamins and minerals, in accordance with the U.S. Recommended Daily Allowance.

METHODS

It is well known that the Nitrogen (N) balance detects small gains or losses of body protein in the whole organism. The N balance has been in use for about 150 years and is one of the mainstays of starvation studies. The N balance, however, only has value when meticulously carried out. Therefore, the following precautions were taken:

(a) To avoid or minimize possible differences in the efficiency of N retention caused by a particular diet sequence, a quintuple cross-over technique was used. This allowed each subject to receive the same five N source diets in different sequences. It was taken into consideration that N retention efficiency is increased by prior lower protein intake;

(b) To avoid common errors in energy intake that could affect the N balance, and to take into consideration the protein sparing effect of carbohydrate, the MESD, G, H, I, J and K diets were supplied a constant energy intake per subject equivalent to 50 Kcal/Kg/day during the study period;

(c) To avoid common errors in N intake that could affect the N balance, the carbohydrate(s) and fats) of the MESD, G, H, I, J and K diets were selected from the essentially protein-free foods of Table III;

(d) To avoid the subjects' N over-intake per mg/Kg/day, which could affect the N balance, the protein requirement was calculated in accordance with the subject's ideal weight; and (e) To avoid over-estimating N intake, caused by unconsumed dietary protein during the MESD, G, H, I, J and K diets, the total consumption of each allotted diet was achieved. All the subject were fed three times per day (8am-2pm-8pm).

In addition, to preserve the double-blind condition of the study, dried bovine milk (diet G), nutrified dried bovine milk (diet H), soybean flour (diet I), and nutrified soybean flour (diet J) and the essential amino acid formula of Table A (diet K) were mixed with an identical fruit shake. The fruit used in the shake was chosen from Table III, and provided each subject with the same energy intake.

Determining Ideal Weight

The subject's ideal weight (in kg) was determined by subtracting factor 100 from the subject's height (in cm), then multiplying the result by either factor 0.9 (man) or 0.8 (woman), in accordance with the subject's sex. The result was rounded off to the nearest 0.500 kg. The following formula was applied:

(a) man's ideal weight$=((H-100)\times 0.9)$ kg; and
(b) woman's ideal weight$=((H-100)\times 0.8)$ kg.

Determining Weight

The subject's weight (in kg) was determined in the early morning before breakfast after the subject's urination and evacuation. The result was rounded off to the nearest 0.100 kg.

Determining N Balance

To determine the subject's N balance, the following formula was applied:

$$B = I - (U + F + S)$$

where:
- B = N balance
- I = N intake
- U = N loss in urine
- F = N loss in feces
- S = N dermal losses.

The N balance represents the difference between N intake (I), and N output (U+F+S); the difference being either positive (N retention, as in active growth), negative (N loss), or zero (N equilibrium). To avoid possible misinterpretation of the subject's daily N balance, which is not commonly linear, the subject's dietary N intake and output were determined during each 2 week period.

Determining N Intake

To determine the subject's N intake (I), the following formula was applied:

Dietary protein amount = Dietary $N \times 6.25$; where use of factor 6.25 implies that the average protein has a 16% N content.

Determining N Output

The subject's urine (U) and feces (F) were collected throughout each 24-hour day of each consecutive 2 week period and the total N was determined by micro-Kjeldahl techniques. To avoid errors in N output, each subject received an enema before starting diet MESD and at the end of diets MESD, G, H, I, J and K. To determine the subject's dermal and minor route losses (S) of N, calculations were made by accepting a constant, it being unusual to make direct measurements of these losses. The following formula was applied:

$$(S) = 5 \text{ mg} \times \text{subject weight (kg)} \times \text{day}.$$

To avoid errors, this calculation was made by applying the subject's real weight.

Determining Lean Tissue Loss

The subject's lean tissue loss was determined by multiplying the subject's protein loss by factor 5. The following formula was applied:

$$\text{Lean Tissue} = N(g) \times 6.25 \times 5.$$

To illustrate

The N content of the mixed proteins of the body is 16%. Thus, 1 g of N excreted represents a loss from the body of 6.25 g of mixed proteins. Intracellular protein exists in approximately a 20 to 25% aqueous solution in the lean tissue of the body (the fat-free, connective tissue-free, and bone-free "wet" tissue). Assuming that 1 g of protein is associated with 5 g of hydrated lean tissue, then 1 g of excreted N represents a loss of $1 \times 6.25 \times 5 = 31.25$ g of lean tissue.

Data Analysis

The data were analyzed using the analysis of variance (ANOVA) followed by the Student-Newman-Keuls test.

Results a. Nitrogen Balance

Table IV summarizes the N balance results of groups 1, 2, 3, 4 and 5 while receiving 64 mg/Kg/day of Nitrogen intake during diets G, H, I, J and K. Table V summarizes the N balance results of all thirty subjects while receiving diets G, H, I, J and K.

The comparison of the mean N output differences within groups 1, 2, 3, 4 and 5 between diets G, H, I, J and K, was statistically significant (P←0,001) in each case.

The comparison of the mean N output differences by each diet (G, H, I, J and K), between groups, was not statistically significant in each case.

b. Efficacy (Tables IV and V)

All five groups, while receiving diet K, regardless of the sequence order, showed the lowest N output with a resulting significantly higher Net Nitrogen Utilization (NNU) (P←0,001) and achieved zero (equilibrium) in their N balances.

The variance related to the mean N output of the subjects receiving diet K points out extremely low and constant values (SD=0,001). This indicates the formula of Table A has a higher NNU in comparison with the other diets.

c. Safety and Tolerance

While receiving diet K none of the thirty subjects reported any side effects, and none showed adverse effects on blood parameters.

During this study, all thirty subjects achieved zero (equilibrium) N balance while receiving diet K in the amount of 0.4 g/kg/day, equivalent to 64 mg/Kg/day of N per subject. Since zero N balance could be achieved at the expense of a slowing of body protein turnover, the attainment of zero N balance does not, in itself, permit the conclusion that the intake of 0.4 g/Kg/day of the formula of Table A, equivalent to 64 mg/Kg/day of N per subject, was nutritionally adequate.

Despite the fact that the subjects received diets consisting of an identical composition of equal amounts of protein or amino acids, carbohydrate(s), fat(s), vitamins and minerals, all thirty subjects showed:

(a) the highest mean NNU while receiving diet K, achieving zero N balance (Tables V and VI);

(b) a lower mean NNU while receiving the nutrified dried bovine milk (diet H), achieving negative N balance, with a mean N loss of 14.0 mg/kg/day (SD=0.2) (Table V), which is 22% lower NNU than while receiving the formula of Table A (Table VI). This mean N loss is equivalent to a lean tissue loss of 437.5 mg/Kg/day;

(c) a lower mean NNU while receiving a nutrified soybean flour (diet J), achieving negative N balance, with a mean N loss of 16.5 mg/Kg/day (SD=0.2) (Table V), which is 26% lower NNU than while receiving the formula of Table A (Table VI). This mean N loss is equivalent to a lean tissue loss of 515.6 mg/Kg/day;

(d) a lower mean NNU while receiving dried bovine milk (diet G), achieving negative N balance, with a mean N loss of 35.3 mg/kg/day (SD=0.2) (Table V), which is 55% lower NNU than while receiving the formula of Table A (Table VI). This mean N loss is equivalent to a lean tissue loss of 1,103.1 mg/kg/day; and (e) the lowest mean NNU while receiving soybean flour (diet I), achieving negative N balance, with a mean N loss of 43.5 mg/kg/day (SD=0.3) (Table V), which is 68% lower NNU than while receiving the formula of Table A (Table VI). This mean N loss is equivalent to a lean tissue loss of 1,359.3 mg/kg/day.

The comparative results showed that the subjects achieved:

(a) 73% higher mean NNU while receiving a nutrified bovine milk (diet H) than while receiving bovine milk (diet G) (Tables V and VI); and (b) 131% higher mean NNU while receiving a nutrified soybean flour (diet J) than while receiving soybean flour (diet I) (Tables V and VI).

The significantly higher mean NNU achieved while receiving a nutrified bovine milk, and/or a nutrified soybean flour, confirm the efficacy of nutrification of food proteins by the appropriate nutrificators to improve the proteins' nutritional value. It can, therefore, be concluded that the high efficacy and safety of the present invention makes it unique for unlimited applications in the nutrification of food proteins.

TABLE I

| GROUP | CHARACTERISTICS | MEAN | S.D. | RANGE |
|---|---|---|---|---|
| 1 | Age (years) | 26 | 5 | 24–36 |
|   | Height (cm) | 163 | 7 | 154–170 |
|   | Ideal Weight (kg) | 54.0 | 8.8 | 43.0–63.0 |
| 2 | Age (years) | 29 | 4 | 24–35 |
|   | Height (cm) | 163 | 10 | 149–174 |
|   | Ideal Weight (kg) | 53.7 | 11.8 | 39.0–66.5 |
| 3 | Age (years) | 27 | 6 | 22–38 |
|   | Height (cm) | 164 | 8 | 149–170 |
|   | Ideal Weight (kg) | 54.3 | 9.6 | 39.0–63.0 |
| 4 | Age (years) | 26 | 5 | 23–36 |
|   | Height (cm) | 162 | 8 | 148–171 |
|   | Ideal Weight (kg) | 53.3 | 9.8 | 38.5–64.0 |
| 5 | Age (years) | 26 | 4 | 22–34 |
|   | Height (cm) | 164 | 11 | 149–174 |
|   | Ideal Weight (kg) | 55.0 | 12 | 39.0–66.5 |

TABLE II

Sequence of the Diets by Group and Period

| DIET | PERIOD | GROUP 1 | GROUP 2 | GROUP 3 | GROUP 4 | GROUP 5 |
|---|---|---|---|---|---|---|
| Preliminary Diet | 30 days | MESD | MESD | MESD | MESD | MESD |
| First Diet | 14 days | G | H | I | J | K |
| Second Diet | 14 days | H | I | J | K | G |
| Third Diet | 14 days | I | J | K | G | H |
| Fourth Diet | 14 days | J | K | G | H | I |
| Fifth Diet | 14 days | K | G | H | I | J |

TABLE III

| Essentially Protein-free Carbohydrate and Fat Foods | | |
|---|---|---|
| Food (100 g) | Protein | Energy |
| Sugar | 0.0 | 384 |
| Corn Oil | 0.0 | 884 |
| Apricot | 0.8 | 57 |
| Pineapple | 0.4 | 52 |
| Peach | 0.8 | 52 |
| Strawberry | 0.8 | 36 |
| Pondapple | 0.4 | 52 |
| Tangerine | 0.7 | 43 |
| Mango | 0.5 | 59 |
| Apple | 0.3 | 58 |
| Muskmelon | 0.5 | 25 |
| Orange | 0.7 | 50 |
| Loquat | 0.2 | 44 |
| Papaya | 0.5 | 32 |
| Pear | 0.3 | 56 |
| Watermelon | 0.5 | 22 |
| Celery | 0.8 | 19 |
| eggplant | 1.0 | 27 |
| Waxgourd | 0.5 | 14 |
| Chayote | 0.9 | 31 |
| Lettuce | 1.0 | 13 |
| cucumber | 0.7 | 15 |
| Ripe Tomato | 0.8 | 21 |
| Sweet Cassava | 1.0 | 132 |
| Carrot | 0.8 | 41 |

TABLE IV

Nitrogen Balance (mg/kg/day) Results by Group and Diet

| GROUP | DIET | N OUTPUT MEAN | S.D. | N BALANCE (*) MEAN | S.D. |
|---|---|---|---|---|---|
| 1 | G | 99.2 | 0.2 | −35.2 | 0.2 |
|   | H | 78.1 | 0.2 | −14.1 | 0.2 |
|   | I | 107.6 | 0.3 | −43.6 | 0.3 |
|   | J | 80.6 | 0.2 | −16.6 | 0.2 |
|   | K | 63.998 | 0.001 | 0.002 | 0.001 |
| 2 | H | 78.0 | 0.2 | −14.0 | 0.2 |
|   | I | 107.3 | 0.2 | −43.3 | 0.2 |
|   | J | 80.4 | 0.1 | −16.4 | 0.1 |
|   | K | 63.998 | 0.001 | 0.002 | 0.001 |
|   | G | 99.2 | 0.1 | −35.2 | 0.1 |
| 3 | I | 107.6 | 0.1 | −43.6 | 0.1 |
|   | J | 80.5 | 0.2 | −16.5 | 0.2 |
|   | K | 63.997 | 0.001 | 0.003 | 0.001 |
|   | G | 99.3 | 0.2 | −35.3 | 0.2 |
|   | H | 77.9 | 0.2 | −13.9 | 0.2 |
| 4 | J | 80.6 | 0.4 | −16.6 | 0.4 |
|   | K | 63.997 | 0.001 | 0.003 | 0.001 |
|   | G | 99.4 | 0.2 | −35.4 | 0.2 |
|   | H | 78.0 | 0.2 | −14.0 | 0.2 |
|   | I | 107.7 | 0.2 | −43.7 | 0.2 |
| 5 | K | 63.998 | 0.001 | 0.002 | 0.001 |
|   | G | 99.3 | 0.2 | −35.3 | 0.2 |
|   | H | 78.0 | 0.4 | −14.0 | 0.4 |
|   | I | 107.4 | 0.2 | −43.4 | 0.2 |
|   | J | 80.6 | 0.2 | −16.6 | 0.2 |

(*) N BALANCE = N INTAKE (64 mg/Kg/day) − N OUTPUT

TABLE V

Nitrogen Balance (mg/kg/day) (All 30 Subjects)

| DIET | N | MEAN | S.D. |
|---|---|---|---|
| G | I | 64 | |
|   | O | 99.3 | 0.2 |
|   | B | −35.3 | 0.2 |
| H | I | 64 | |
|   | O | 78.0 | 0.2 |
|   | B | −14.0 | 0.2 |
| I | I | 64 | |
|   | O | 107.5 | 0.3 |
|   | B | −43.5 | 0.3 |
| J | I | 64 | |
|   | O | 80.5 | 0.2 |
|   | B | −16.5 | 0.2 |
| K | I | 64 | |
|   | O | 63.997 | 0.001 |
|   | B | 0.003 | 0.001 |

I = N INTAKE; O = N OUTPUT; B = N BALANCE

TABLE VI

Net Nitrogen Utilization (NNU) by Diet

| DIET | NNU | N/LOSS |
|---|---|---|
| G | 45% | 55% |
| H | 78% | 22% |
| I | 32% | 68% |
| J | 74% | 26% |
| K | 100% | 0% |

I claim:

1. A method of increasing the protein nutritional value of a food in order to prepare a nutrified food product, said method comprising:
(a) determining the content of essential amino acids in said food;
(b) adding to said food an amount of essential amino acids to form a nutrified food product having for each 10 grams of essential amino acids the following amounts of essential amino acids:
   (a) from 0.608 g. to 2.470 g. isoleucine;
   (b) from 0.913 g. to 4.102 g. leucine;
   (c) from 0.630 g. to 3.538 g. lysine;
   (d) from 0.116 g. to 1.167 g. methionine;
   (e) from 0.421 g. to 1.971 g. phenylalanine;
   (f) from 0.485 g. to 1.930 g. threonine;
   (g) from 0.104 g. to 0.700 g. tryptophan; and
   (h) from 0.630 g. to 2.850 g. valine.

2. A method as defined in claim 1, wherein the food is derived from a vegetable source.

3. A method as defined in claim 1, wherein the food is derived from an animal source.

4. A method as defined in claim 2, wherein said food is selected from the group consisting of wheat flour, soybean flour, oat flour, corn flour, amaranth flour, nut flours, potato flour and rice flour or mixtures thereof.

5. A method as defined in claim 3, wherein said food is derived from milk.

6. A method as defined in claim 1, wherein vitamins and minerals are added to said food.

7. A method as defined in claim 1, wherein a protein free carbohydrate is added to the nutrified product.

8. A method as defined in claim 7, wherein a highly polyunsaturated vegetable fat is added to the nutrified product.

9. A nutrified product produced by the process of claim 1

10. A nutrified product produced by the process of claim 4.

11. A nutrified product produced by the process of claim 5.

12. A nutrified product produced by the process of claim 7.

13. A nutrified product produced by the process of claim 8.

14. A method of increasing the protein nutritional value of a food in order to prepare a nutrified food product, said method consisting essentially of the steps of:
(a) determining the content of essential amino acids in said food;

(b) adding to said food an amount of essential amino acids to form a nutrified food product having for each 10 grams of essential amino acids the following amounts of essential amino acids:
 (a) from 0.608 g. to 2.470 g. isoleucine;
 (b) from 0.913 g. to 4.102 g. leucine;
 (c) from 0.630 g. to 3.538 g. lysine;
 (d) from 0.116 g. to 1.167 g. methionine;
 (e) from 0.421 g. to 1.971 g. phenylalanine;
 (f) from 0.485 g. to 1.930 g. threonine;
 (g) from 0.104 g. to 0.700 g. tryptophan; and
 (h) from 0.630 g. to 2.850 g. valine.

* * * * *